(12) United States Patent
Wilson et al.

(10) Patent No.: US 6,870,686 B2
(45) Date of Patent: Mar. 22, 2005

(54) STACK OF CLEAR LAMINATED REMOVABLE LENSES FOR REDUCING SURFACE DRAG ON AIRFIOILS

(76) Inventors: Bart Wilson, 1218 Puerta Del Sol, San Clemente, CA (US) 92673; Seth Wilson, 1218 Puerta Del Sol, San Clemente, CA (US) 92673; Stephen S. Wilson, 1218 Puerta Del Sol, San Clemente, CA (US) 92673

( * ) Notice: Subject to any disclaimer, the term of this patent is extended or adjusted under 35 U.S.C. 154(b) by 0 days.

(21) Appl. No.: 10/760,806

(22) Filed: Jan. 20, 2004

(65) Prior Publication Data

US 2004/0145813 A1 Jul. 29, 2004

Related U.S. Application Data

(63) Continuation-in-part of application No. 10/050,366, filed on Jan. 16, 2002, now abandoned, which is a continuation of application No. 09/449,318, filed on Nov. 24, 1999, now Pat. No. 6,388,813.

(51) Int. Cl.[7] .............................. G02B 3/00; G02B 33/00
(52) U.S. Cl. ...................................... 359/642; 428/42.17
(58) Field of Search ................................. 359/359, 630, 359/631, 642; 2/9, 15, 424–435; 351/44, 47; 428/42.17

(56) References Cited

U.S. PATENT DOCUMENTS

| | | |
|---|---|---|
| 2,511,329 A | 6/1950 | Craig |
| 3,785,102 A | 1/1974 | Amos |
| 4,076,373 A | 2/1978 | Moretti |
| 4,090,464 A | 5/1978 | Bishopp et al. |
| 4,138,746 A | 2/1979 | Bergmann |
| 4,301,193 A | 11/1981 | Zuk |
| 4,332,861 A | 6/1982 | Franz et al. |
| 4,380,563 A | 4/1983 | Ayotte |
| 4,716,601 A | 1/1988 | McNeal |
| 4,842,919 A | 6/1989 | David et al. |
| 5,002,326 A | 3/1991 | Westfield et al. |
| 5,104,929 A | 4/1992 | Bilkadi |
| 5,194,293 A | 3/1993 | Foster |
| 5,420,649 A | 5/1995 | Lewis |
| 5,443,877 A | 8/1995 | Kramer et al. |
| 5,512,116 A | 4/1996 | Campfield |
| 5,592,698 A | 1/1997 | Woods |
| 5,633,049 A | 5/1997 | Bilkadi et al. |
| 5,671,483 A | 9/1997 | Reuber |
| 5,740,560 A | 4/1998 | Muoio |
| 5,972,453 A | 10/1999 | Akiwa |
| 6,085,358 A | 7/2000 | Cogan |
| 6,461,709 B1 | 10/2002 | Janssen et al. |
| 6,536,045 B1 | 3/2003 | Wilson et al. |

FOREIGN PATENT DOCUMENTS

| | | |
|---|---|---|
| DE | 3637 188 A1 | 10/1986 |
| EP | 0 671 258 A2 | 2/1995 |
| GB | 2310862 A | 3/1997 |
| JP | 62-53832 | 5/1961 |
| JP | 10-167765 | 2/1997 |

Primary Examiner—Ricky Mack
(74) Attorney, Agent, or Firm—Stetina Brunda Garred & Brucker

(57) ABSTRACT

A stack of laminated transparent lenses consists of two alternating optically clear materials in intimate contact. The materials are a plastic lens and clear adhesive. The adhesive is uninterrupted. The lens and the adhesive have refraction mismatch of less than 0.2. A tab portion is part of each lens acts as an aid in peeling way the outermost lens after contamination of the lens layer during racing conditions. The lens stack can be mounted to the posts on the face shield or laminated directly to a windshield. The lens stack can be applied to an airfoil. During a race, as mud and dirt are accumulated, the top lens of the lens stack on the airfoil can quickly be removed revealing the next (clean) lens in the stack.

19 Claims, 6 Drawing Sheets

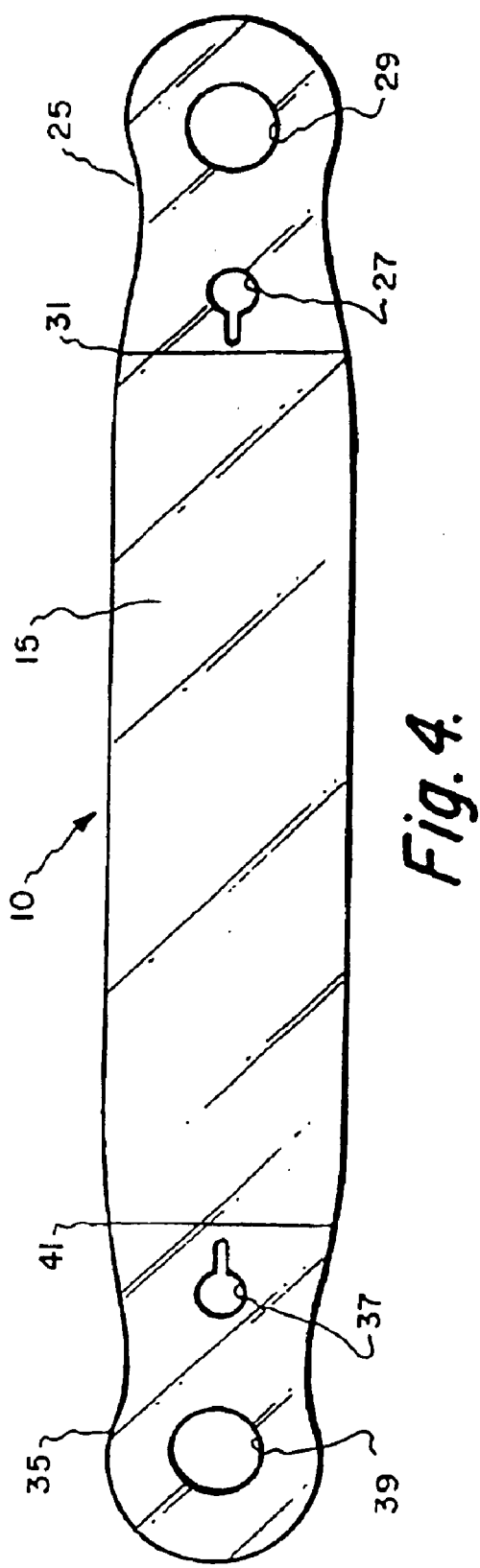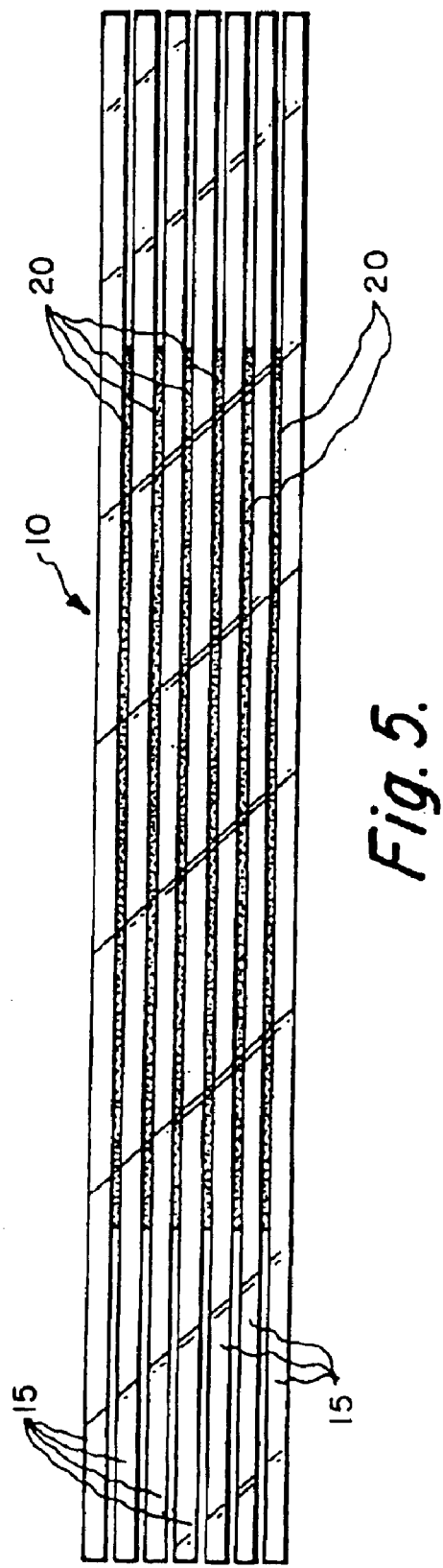

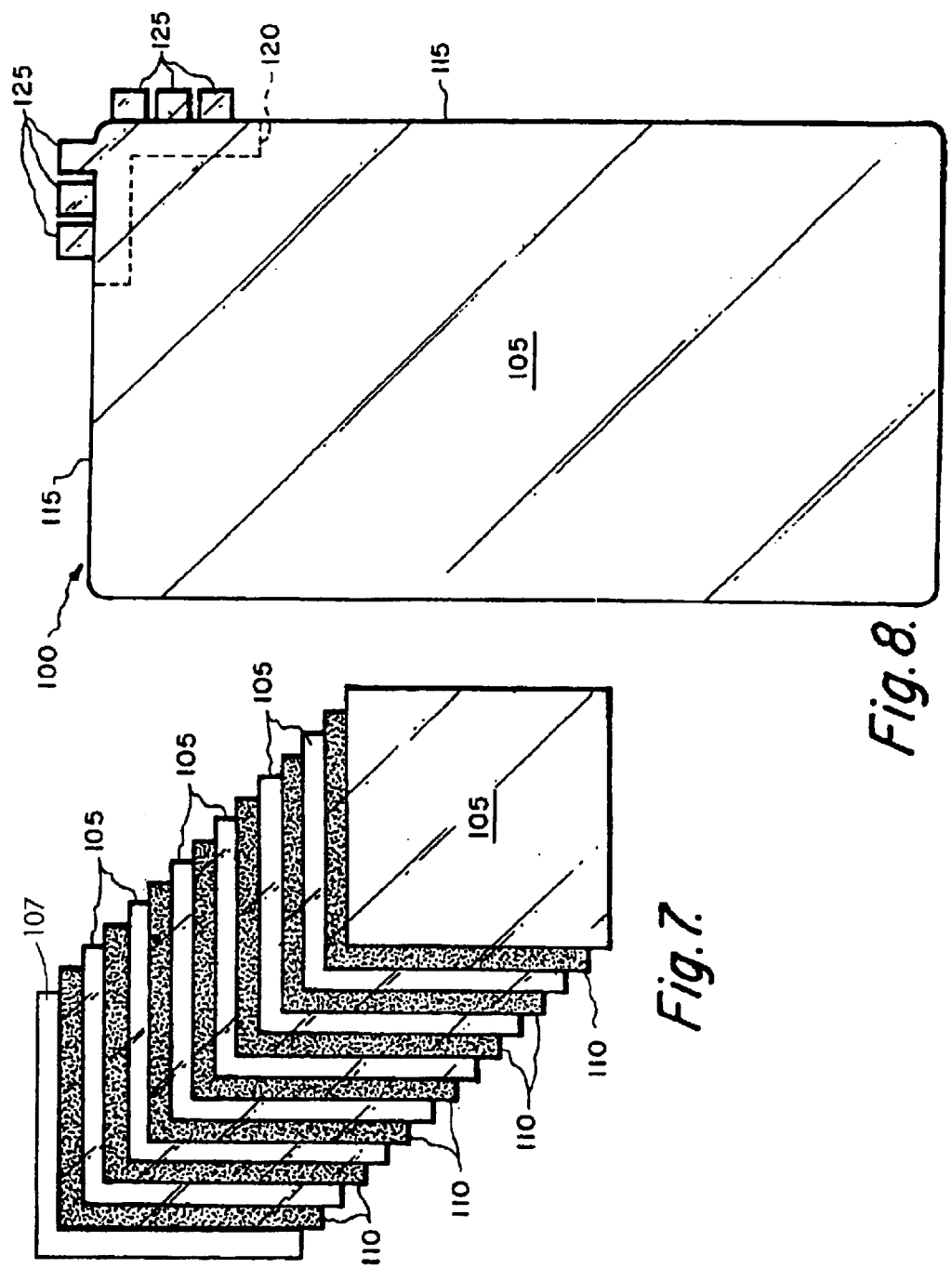

STACK OF CLEAR LAMINATED REMOVABLE LENSES FOR REDUCING SURFACE DRAG ON AIRFIOILS

CROSS-REFERENCE TO RELATED APPLICATIONS

This application is a continuation-in-part of U.S. application Ser. No. 10/050,366 filed Jan. 16, 2002, now abandoned the entire contents of which are incorporated by reference herein, which is a continuation of U.S. application Ser. No. 09/449,318 filed Nov. 24, 1999, now U.S. Pat. No. 6,388,813, the entire contents of which are incorporated by reference herein.

STATEMENT RE: FEDERALLY SPONSORED RESEARCH/DEVELOPMENT

Not Applicable

BACKGROUND OF THE INVENTION

The present invention relates generally to airfoils and more particularly to a stack of clear laminated removable lens for reducing surface drag on airfoils while allowing for the viewing of advertising graphics on the airfoils.

Face shields are employed in environments where contamination of the eyes may occur. It is well known in the art that flexible transparent lenses affixed by numerous methods are overlaid on the face shield for protection. The lenses are easily removed and discarded when visibility is reduced from the accumulation of dirt or other contaminants. In motor sports for instance, multiple layers of transparent lenses are overlaid on the face shield, each being sequentially removed as they become contaminated, because they reduce the visibility of the operator. The drawback of the lenses in the prior art is that each transparent lens applied over the face shield is itself a hindrance to good visibility due to its optical index of refraction. Most common materials used as plastics have optical indexes of refraction ranging from 1.47 to 1.498. The index mismatch between the removable lens and air (air has an optical index of 1.00) causes a reflection of 4% of the light that would normally come to the operator's eyes. This reflection effect is additive for each additional surface to air interface. Then for each removable lens having two surfaces, the reflections are 8%. Thus a stack of seven lenses would reflect 42% of the light away from the operator thereby reducing the brightness of the objects viewed. A second optical phenomenon occurs simultaneously that also reduces visibility. The reflections are bi-directional and thus make the lens stack appear as a semi-permeable mirror to the operator. This mirror effect further reduces visibility, because the light that passes through the lens stack reflects off of the operator's face and then reflects off of the lens stack into the operator's eyes. The effect to the operator is that he sees his own image on the inside of the stack nearly as brightly as the objects viewed on the outside. This significantly reduces visibility.

Another drawback to this stacking arrangement is that moisture exhaled by the operator's breath can cloud or fog-up the lenses also reducing visibility. The air spaces between each lens allow the moisture to enter this area.

Airfoils are commonly used on racecars to create down force which improves the traction of the car. In dirt car racing, the airfoil can be as large as sixteen square feet. Most of this area is covered with advertising graphics.

As described above, dirt and mud accumulate on a driver's goggles during a race is a significant problem. Such an accumulation of dirt and mud is not limited to a driver's goggles. The dirt and mud accumulates over the entire vehicle. Such an accumulation of dirt and mud can be a particular problem on airfoils. The airfoils accumulate heavy mud and dirt which both reduces the efficiency of the airfoils and covers up the advertising graphics on the airfoils. Another drawback of current airfoils is drag that is created by the airfoil shape, attitude and the surface finish of the airfoil. Part of this surface drag problem is created by imperfections in the airfoil such as rivets and joints.

Therefore, there is a need for a way to quickly clean accumulated mud and dirt from an airfoil so as to reduce the surface drag caused by the accumulated mud and dirt as well as to allow for the viewing of any advertising graphics on the airfoil.

BRIEF SUMMARY OF THE INVENTION

An object of the present invention is to provide a series of easily removable optically clear lens stacks that do not cause reflection to the operator's eyes. The prior art discloses reflective lens stacks that do cause reflections to the operator's eyes. An example of this type of prior art of reflective lens stack is disclosed in U.S. Pat. No. 5,592,698 issued on Jan. 14, 1997 to Woods.

Refraction is the change in the direction in which waves travel when they pass from one kind of matter to another. Waves are refracted (bent) when they pass at an angle from one medium into another in which the velocity of light is different. The amount that a ray of a certain wavelength bends in passing from one medium to another is indicated by the index of refraction between the two mediums for that wavelength. The index of refraction indicates the amount that a light ray bends as it passes out of one substance and into another. When light passes from air to a denser substance, such as Mylar film, it slows down. If the light ray enters the Mylar film at any angle except a right angle, the slowing down causes the light ray to bend at the point of entry. This bending is called refraction. The ratio of the speed of light in air to its speed in the Mylar film is the Mylar film's index of refraction.

The present invention includes a series of alternating optically clear films whose indexes of refraction are matched to within 0.2 and which will nearly eliminate all reflections to the operator's eyes. The layers of film are adhesively laminated to one another and are compliant so there is no air between the layers. The film layers can be large and generally rectangular in shape with a tab extending from each of the film layers. The tabs can be staggered so that the user can remove the top most layer and then the next succeeding layer. This embodiment of the present invention can be applied to race car windshields, windows, visors or direct view displays such as ATM machines that are subject to contaminating environments. Accordingly, the present invention is an adhesively laminated multi-layered clear film adapted to be used on a racer's face shield, or on the windshield of a race car to keep the viewing area clean during the course of a race.

Another embodiment is similar to that just described except that the stack of clear laminated lenses is applied to a vehicle (e.g., race car) airfoil. During a race, as mud and dirt are accumulated, the top lens of the lens stack on the airfoil can quickly be removed revealing the next (clean) lens in the stack. This quick elimination of the dirty top lens improves the surface drag that was reduced by the accumulated dirt and mud. The clear stack of lenses allows advertising graphics on the airfoil to be visible. As mud and dirt are accumulated on the airfoil, the advertising graphics become partially or even completely obscured. Removal of the top (dirty) lens restores the visibility of the advertising graphics. Furthermore, surface drag on an airfoil is reduced by imperfections on the wing that affect the smoothness of the airfoil surface, such as rivets and joints. The stack of laminated lenses helps to smooth the wing surface, minimizing such imperfections and reducing the surface drag that was caused by such imperfections.

BRIEF DESCRIPTION OF THE DRAWINGS

These as well as other features of the present invention will become more apparent upon reference to the drawings wherein:

FIG. 4 is a front elevational view illustrating the present invention before it is affixed to the face shield of the helmet.

FIG. 5 is a top view of the stackable lenses illustrating seven layers of lens held together by an adhesive applied between each lens with the thickness of the layers of each lens and applied adhesive highly exaggerated to clearly show the relationship between the lenses and the adhesive and also to show the end portions that do not have any adhesive between each lens layer for forming the removable tab portions at both ends of the present invention.

FIG. 7 is an exploded perspective view illustrating seven sheets of film layer and seven layers of clear adhesive interposed between each sheet of film layer. This embodiment is used for windshields, windows and the like.

FIG. 8 is a view of the laminated sheets illustrated in FIG. 7 having a rectangular shape with a series of six tabs for removing each top layer of the lenses successively as the uppermost exposed lens layer becomes soiled or otherwise contaminated.

DETAILED DESCRIPTION OF THE INVENTION

Figure 9:
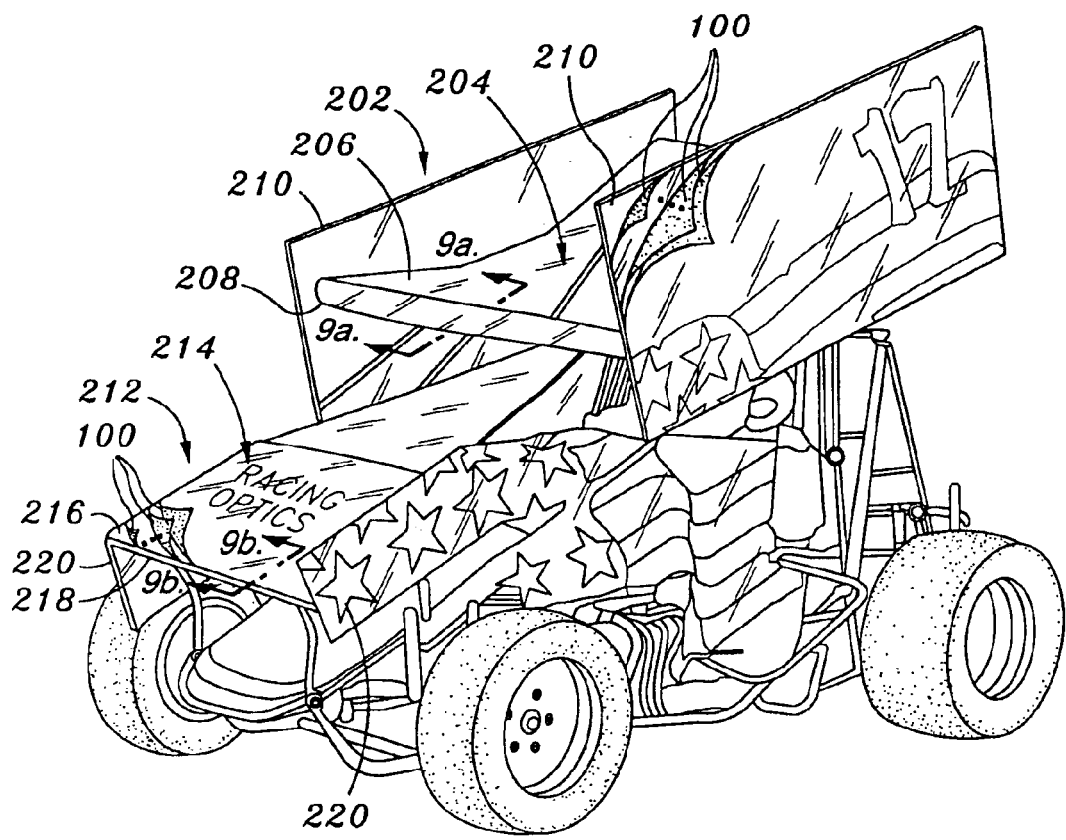
FIG. 9 illustrates a race car having airfoils with the sheets of film layer and adhesive shown in FIG. 7 attached to the airfoils.

Referring now to the drawings wherein the showings are for purposes of illustrating preferred embodiments of the present invention only, and not for purposes of limiting the same, several embodiments are illustrated. A first embodiment shown in FIGS. 1–4 illustrates a stack of laminated transparent lenses that can be affixed to a face shield on a helmet, FIGS. 7–8 illustrate an embodiment where the stack of lenses are affixed to a windshield by wetting the bottom adhesive layer and mounting it directly on the windshield, FIG. 9 illustrates an embodiment where the stack of lenses is mounted on an airfoil to reduce surface drag due to imperfections on the airfoil as well as to quickly remove accumulated dirt and mud.

Figure 3:
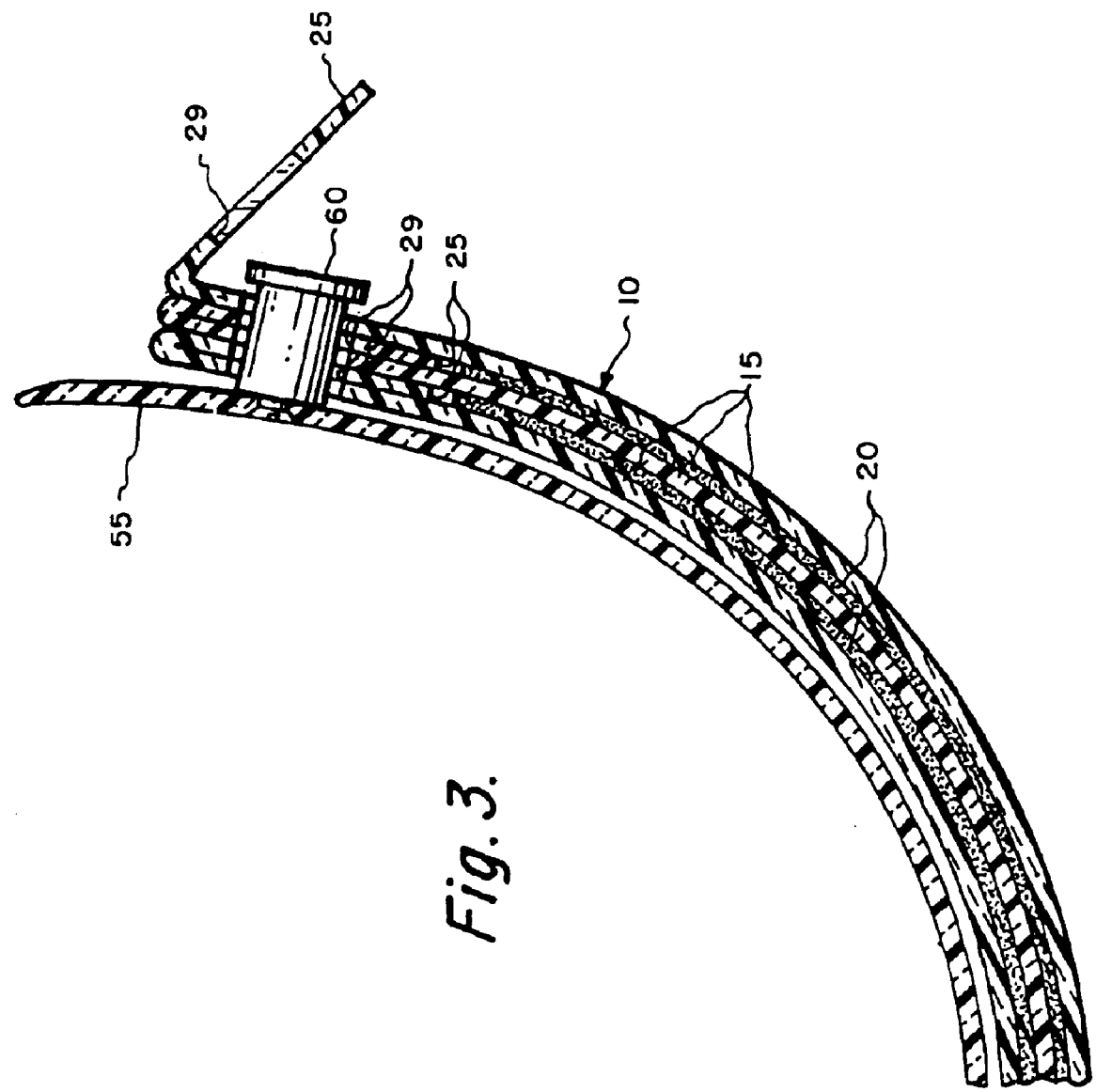
FIG. 3 is a partial sectional view taken along line 3 in FIG. 2. This view shows the tension post extending outwardly from the face shield with the left-side end tab portion of the present invention.

In the first embodiment shown and described, a stack of laminated transparent lenses is affixed to a face shield of a helmet. FIG. 4 is a front elevational view illustrating the present invention 10 before it is affixed to the face shield of the helmet. The top view in FIG. 5 illustrates seven layers of lenses 15 adhesively affixed to each successive lenses. The adhesive layer is numbered 20. The material used to form the lenses is preferably a clear polyester. The lens layers are fabricated from sheets of plastic film sold under the registered trademark Mylar owned by the DuPont Company. The several trademark registrations for the mark Mylar list several types of products sold under that mark, and include polyester film. The type of Mylar used in the present invention is made from the clear polymer polyethylene terephalate, commonly referred to as PET, which is the most important polyester. PET is thermoplastic—that is, it softens and melts at high temperatures. Uses of PET film include magnetic tapes and shrink wrap. The adhesive 20 used to laminate the lenses together sequentially is a clear optical low tack material. The thickness of each lens will range from 0.5 mil to 7 mil (1 mil is 0.001"). The preferred thickness will be 2 mil. Even after the adhesive material is applied to a 2 mil thickness lens, the thickness of the 2 mil thickness lenses will still be 2 mil. The adhesive has nominal thickness. As will be apparent to those of ordinary skill in the art, such nominal thickness of the adhesive is about 2 microns. As illustrated in FIG. 5, after the seven layers of film and the six layers of adhesive are laminated together, the overall thickness of the end product is 15 mils. The term "wetting" can be used to describe the relationship between the laminated film layers. When viewing through the laminated layers, it appears to be one single piece of plastic film. No reflections are evident. The end tab portions without the adhesive exhibit reflections are not a hindrance to the user, because these end portions are folded back over the posts as illustrated in FIG. 3, and do not affect the visibility of the user.

The adhesive material 20 will be a water-based acrylic optically clear adhesive or an oil based clear adhesive, with the water based adhesive being the preferred embodiment. After the seven layers are laminated or otherwise bonded together with the adhesive layers, the thickness of each adhesive layer is negligible even though the adhesive layers are illustrated in FIGS. 4 and 5 as distinct layers. FIG. 5 is a top view of the stackable lenses illustrating seven layers of lens held together by an adhesive applied between each lens with the thicknesses of the layers of lenses and applied adhesive highly exaggerated to clearly show the relationship between the lenses and the adhesive and also to show the end portions that do not have any adhesive between each lens layer for forming the removable tab portions 25 at both ends of the present invention.

Figure 6:
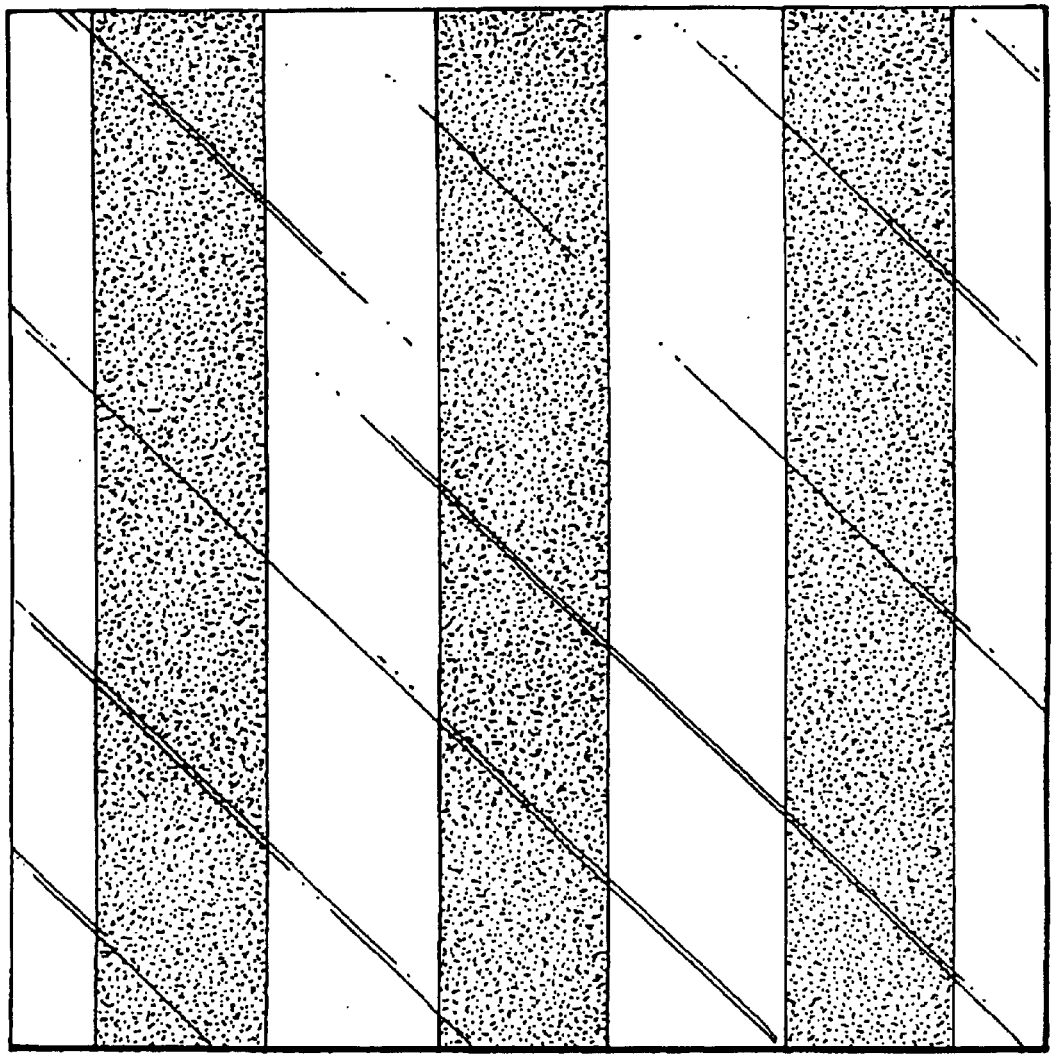
FIG. 6 illustrates a 60" wide roll of film, which will be used to cut out the optical stacks that are illustrated in FIG. 4. The gray stripes illustrate the clear adhesive, and the clear stripes illustrate the clear film without adhesive. It is to be understood that the gray stripes are for illustration purposes only, because the adhesive is clear.

The individual stackable lenses package, illustrated in FIG. 5 for use with racing helmets, can be fabricated from a roll of film as illustrated in FIG. 6. The film in FIG. 6 includes seven layers of clear polyester film, and having the water-based acrylic adhesive laminating the seven film layers to one another. Keep in mind that each layer of the lenses can be easily peeled away as the top layer exposing the next clean lens. Each succeeding lens layer can be removed as the top lens becomes contaminated with dirt and grime during racing conditions.

Figure 2:
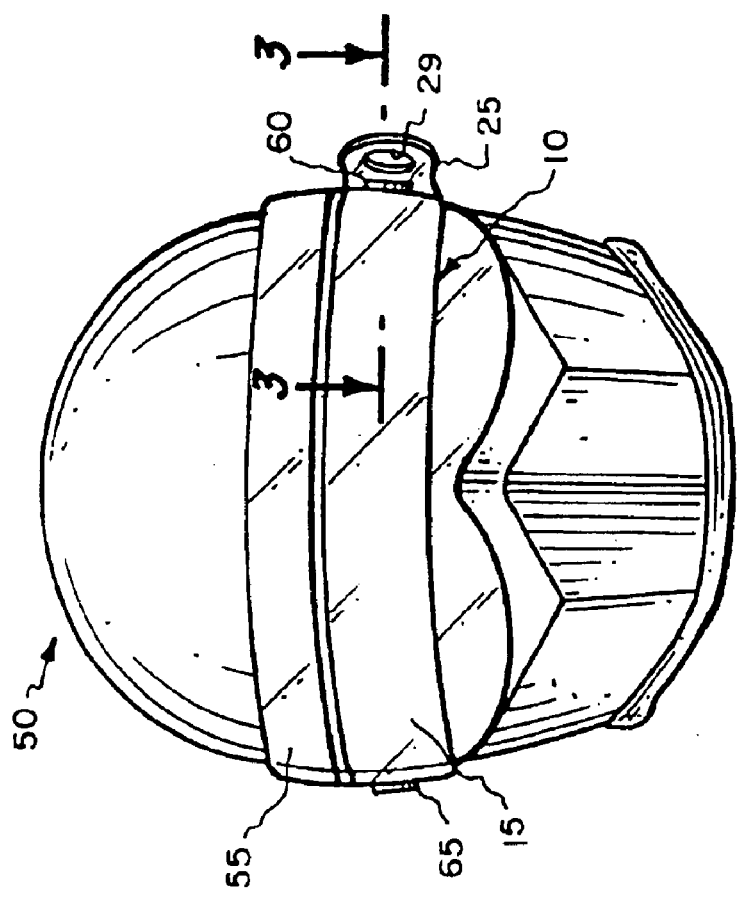
FIG. 2 is a front elevational view of the helmet shown in FIG. 1 showing the tab portion without any adhesive for allowing the wearer of the helmet to easily grasp the tab and peel-off the soiled top layer of the present invention.
Figure 1:
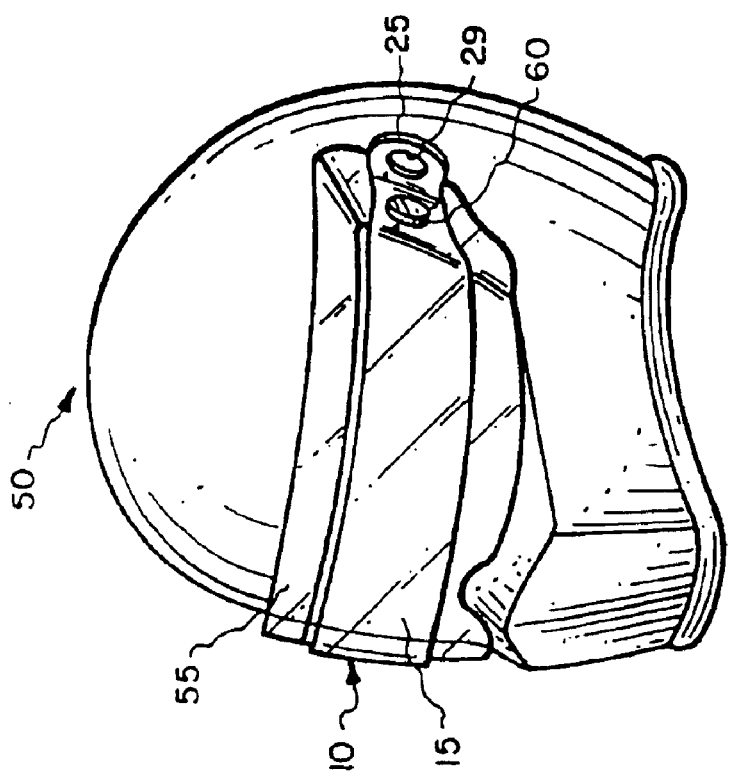
FIG. 1 is a perspective view of an off-road wearer's helmet showing one embodiment of the present invention affixed to the face shield of the helmet.

Referring back now to FIG. 3. As previously stated, FIG. 3 illustrates the tension post 60 extending outwardly from the face shield 55 with the left side end tab portion 25 of the present invention illustrated. The face shield 55 has a left tension post 60 and a right tension post 65. The present invention 10 has the following dimensions: 18" in length; 2½" in height; and about 15 mils in thickness (1 mil is 0.001"). The present invention is symmetrical about its vertical medial axis and about its horizontal medial axis. The left end has a removable tab portion 25, and the right end has a removable tab portion 35. The area 15 indicates where the adhesive 20 is applied to the layers of the lens 15. The bilateral demarcation lines 31 and 41 indicate where the adhesive stops on either side. The demarcation lines 31 and 41 also indicate where the tab portions begin. The present invention has a pair of bilateral keyhole-shaped slots 27 and 37 for demountably engaging the two helmet posts 60 and 65 respectively. The curved distance between the two helmet posts 60 and 65 is the same as the distance between the centers of the pair of slots 27 and 37. The user secures the lenses to the face shield by positioning the slots adjacent the helmet posts and passing the posts through the slots. It is preferable that the remainder of the tab portion outboard from the slot be folded back upon itself so that the finger hole is also passed through the helmet post. This is illustrated in FIG. 3. The proper installation of the present invention on the helmet requires the user to position the bottom lens of the stack through the post hole by passing the post through the slot, then folding back the remainder of the tab portion 25 so that post passes through the finger hole 29. This is done for each lens working from the bottom up until the tab portion 25 of the top lens extends unfolded as illustrated in FIG. 2. In this manner, the helmet wearer can easily put his index finger through the finger hole topmost lens layer. The clean layer below the removed layer is then exposed and the removal tab portion on the exposed layer will spring back to the unfolded position to expose the finger hole so that the helmet wearer can easily remove that layer after it becomes soiled and contaminated. The plastic material forming the lenses is resilient and will spring back to its unfolded position and extend outwardly from the face shield. The thicknesses of the layered lenses and folded tab portions illustrated in FIG. 3 are highly exaggerated to clearly show the folding relationship. In actual practice seven lenses and seven tab portions will be stacked into the space between the end of the post and the outer surface of the face shield. Remember that there is no adhesive between the tab portions. This allows the removal tab portions to fan out. They do not stick to one another.

The present invention as shown in Drawing Figures has removal tab portions at both ends. This allows a right or left-handed person to easily remove the topmost layer. It also allows the driver to pull the tab with either hand depending on the circumstances of the race. It is to be understood that the present invention includes a laminated lenses with only a left tab portion 25, or only a right tab portion 35, or both a left and a right tab portion.

The windshield embodiment 100 illustrated in FIGS. 7 and 8 will now be discussed in detail. An optical stack of removable lenses for affixing to an optical window such as a racing car windshield is disclosed in FIG. 8. The embodiment 100 has a plurality of seven generally rectangular superposed removable lenses 105 adhesively affixed to one another. The outer perimeter is continuous. Each of the removable lens 105 is held to each successive lens with a clear uninterrupted adhesive layer 110 interposed between each of the removable lens. The perimeter has at least one generally straight edge portion 115. In the embodiment illustrated in FIG. 8, the perimeter is rectangular and has four straight edge portions, one for each side. It is to be understood that the invention could be practiced with only one generally straight edge portion. The area adjacent to the straight edge portion 115 has a banded portion 120 that does not have any adhesive affixed to any of the layers of film to assist in allowing each said film layer 105 to be peeled off successively along the straight edge portion. A plurality of staggered tabs 125 are affixed to the film layers one-at-a-time. The tabs 125 extend from the straight edge portions 120 to assist the user in removing the uppermost soiled and grimy film layer, and to successively remove each next clean layer as the top exposed layer becomes contaminated.

The adhesive layer can be foreshortened so as to expose successively a portion of the lens layers without optical wetting to create a grasping tab.

The stack of removable lenses as illustrated in FIGS. 7 and 8 can have an optically clear adhesive as the bottom last layer to aid in mounting the stack of lenses to the windshield. The stack is affixed to the windshield in much the same way that tinted window plastic film is affixed to a window. The windshield is sprayed with water and the bottom adhesive layer with the stack is then applied to the windshield. Air bubbles and the like are eliminated with a squeegee appliance. The bottom layer becomes "wetted" to the windshield.

The stack of removable lenses 100 can be applied to any type of optical window such as windshield, window, face shield, or a video display. It is common at an ATM terminal to have a video display for the customer. The surface of the display can be kept clear by using the present invention.

The clear stack of lenses described herein can also be used for non-window surfaces. One example of such non-window usage is for airfoils, for example, those used on racecars. FIG. 9 shows a race car having two airfoils or wings. The car shown in FIG. 9 has a top airfoil assembly 202 which includes an airfoil 204 and two sideboards 210 attached to the sides of the airfoil 204. The car shown in FIG. 9 also includes a front airfoil assembly 212 which includes an airfoil 214 the and two sideboards 220 attached to the sides of the airfoil 214. The airfoil assemblies 202, 212 are used to create down force in order to improve traction of the car. The majority of the surfaces of airfoils 204, 214 and sideboards 210, 220 are typically covered with advertising graphics as shown in FIG. 9. These advertising graphics may be painted on to the airfoils 204, 214 and sideboards 210, 220 or they may be decals that are adhered to the airfoils 204, 214 and sideboards 210, 220, or they may be a combination of paint and decals that are applied to the airfoils 204, 214 and sideboards 210, 220.

During a race, the airfoils 204, 214 and/or the sideboards 210, 220 become covered with dirt and mud. Such soiling of the airfoils 204, 214 and sideboards 210, 220 obscures the advertising graphics. This soiling of the airfoils 204, 214 and the sideboards 210, 220 also increases surface drag which slows down the vehicle.

If a stack of clear laminated lenses 100, such as the lenses shown in FIG. 7, is applied to the airfoil 204, 214 and/or the sideboards 210, 220, the top lens of the lens stack can quickly and easily be removed leaving the remainder of the stack of clean, clear lenses. In exemplary embodiments, the lenses of the lens stack 100 include tabs 125 such as the lenses shown in FIG. 8. There may be multiple tabs on a given lens. For example, there may be tabs on opposite sides of the lens. In exemplary embodiments, the tabs 125 are staggered like the tabs shown in FIG. 8 to allow for easy grasping of the top tab. If the lenses have tabs 125, the top lens can be grasped by the tab 125 and removed from the stack. Alternatively, instead of a tab 125, the lenses may have a border along at least one edge of the lens which does not have adhesive. Removal of the top, soiled lens can quickly and easily be accomplished when the vehicle is stopped for a pit stop (e.g., to change a tire). After the top, soiled lens is removed, the graphics on the airfoil are again clearly visible. Removal of the soiled top lens also reduces the surface drag which was increased due to the dirt and mud on the top lens.

Figure 9A:
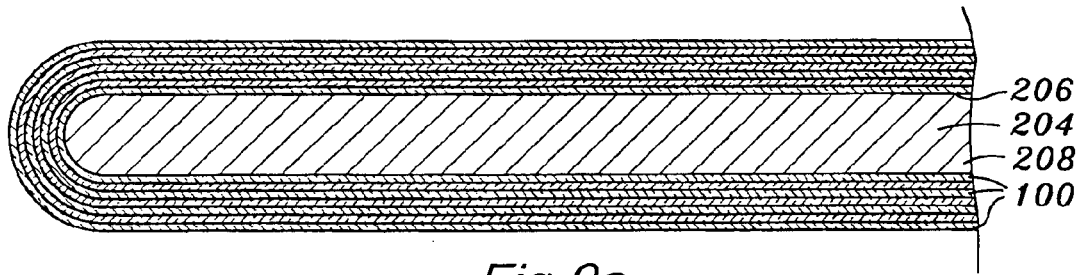
FIG. 9A is a cross sectional view of an airfoil shown in FIG. 9, the airfoil being covered by wrapping the sheets of film layer around an edge of the air foil so that the sheets of film layer cover at lease a portion of the top surface and bottom surface of the airfoil.
Figure 9B:
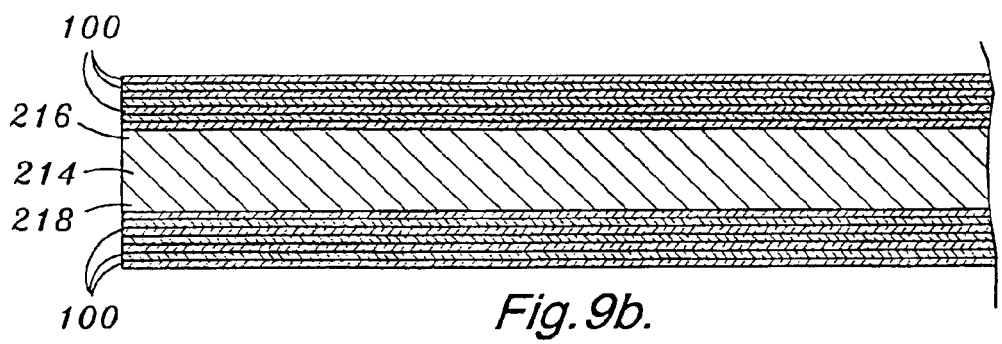
FIG. 9B is a cross sectional view of an airfoil shown in FIG. 9, the airfoil being covered by adhering a stack of sheets of film layer over at least a portion of the top surface and another stack of sheets of film layer over the bottom surface of the airfoil.

As shown in FIG. 9, the lenses may be placed on the top surface of the airfoil 206, 216 and the bottom surface of the airfoil 208, 218. The lenses may cover the airfoil 204 by wrapping the lenses around the airfoil 204 as shown in FIG. 9A or a separate stack of lenses can be placed on the top and bottom surfaces of the airfoil 214 as shown in FIG. 9B.

The surface of an airfoil has imperfections, such as rivets, joints, paint, decals, or some combination thereof. These imperfections also increase the surface drag. Application of the stack of lenses over such imperfections smoothes out the surface of the airfoil thereby reducing the surface drag of the airfoil. The bottom lens of the stack 100 may be adhered to the airfoil 204, 214 and/or sideboards 210, 220 using "wetting" as described above.

Herein in what is conceived to be the best mode contemplated, it is recognized that departures may be made therefrom within the scope of the invention which is therefore not to be limited to the details disclosed herein, but is to be afforded the full scope of the invention.

What is claimed is:

1. A stack of laminated removable lenses for affixing to an airfoil comprising an airfoil top surface, the stack of laminated removable lenses comprising:

a plurality of superposed removable lenses adhesively affixed to one another, the plurality of superposed removable lenses including a top lens and bottom lens;

each said removable lens being held to each successive lens with a uninterrupted adhesive layer interposed between each said removable lens, the bottom lens configured to be affixed to the airfoil top surface.

2. The stack of laminated removable lenses recited in claim 1, wherein if the top lens of the stack of laminated removable lenses affixed to the airfoil becomes soiled, the top lens can be removed from the stack of laminated removable lenses exposing a clear lens beneath the removed lens such that the airfoil top surface is clearly visible beneath the stack of laminated removable lenses affixed thereto.

3. The stack of laminated removable lenses recited in claim 2, wherein the airfoil top surface includes graphics thereon, the graphics being clearly visible beneath the stack of laminated lenses affixed thereto after removal of the soiled top lens.

4. The stack of laminated removable lenses recited in claim 1, wherein if the top lens becomes soiled, the top lens can be removed from the stack of laminated removable lenses such that if the stack of laminated lenses is affixed to the airfoil top surface, the surface drag is reduced when the soiled top lens is removed.

5. The stack of laminated removable lenses recited in claim 1, wherein the bottom lens of the stack of removable lenses is affixed to the airfoil top surface by wetting an adhesive layer on the bottom lens directly to the airfoil top surface.

6. The stack of laminated removable lenses as recited in claim 5, further comprising a temporary removable sheet cover temporarily affixed to the adhesive layer on the bottom lens to protect the adhesive layer on the bottom lens until the temporary removable sheet cover is removed so that the stack of removable lenses can be affixed to the airfoil top surface.

7. The stack of laminated removable lenses recited in claim 1, wherein the removable lenses are generally rectangular.

8. The stack of laminated removable lenses as recited in claim 7, wherein the removable lenses form a continuous perimeter having a generally straight edge portion.

9. The stack of laminated removable lenses as recited in claim 7, wherein an area adjacent the straight edge portion has a banded portion that does not have any adhesive affixed to any of the layers of film to assist in allowing the film layer to be peeled off successively along the straight edge portion.

10. The stack of laminated removable lenses recited in claim 1, wherein said removable lenses are made of a Mylar material.

11. The stack of laminated removable lenses recited in claim 1, wherein each said lens has a removable tab portion on at least one end which does not have any adhesive layer on either side of said tab portion for allowing a user to quickly grasp said removable tab portion for removing the top lens and exposing a clean lens directly underneath said removed top lens.

12. The stack of laminated removable lenses recited in claim 11 further comprising: a second removable tab portion opposite the end of said removal tab portion.

13. The stack of laminated removable lenses recited in claim 1, wherein when the bottom lens is affixed to the airfoil top surface the bottom lens covers imperfections in surface smoothness of the airfoil top surface.

14. The stack of laminated removable lenses recited in claim 1, wherein each of the lenses has a thickness of 0.5 mil. to 7 mil.

15. The stack of laminated removable lenses recited in claim 1, wherein each of the lenses has a thickness of about 2 mil.

16. The stack of laminated removable lenses recited in claim 1, wherein each said removable lens is held to each successive lens with the uninterrupted adhesive layer interposed between each said removable lens such that there are no evident reflections when looking through the stack of laminated removable lenses.

17. The stack of laminated removable lenses recited in claim 1, wherein each said removable lens is held to each successive lens with a clear uninterrupted adhesive layer of negligible thickness interposed between each said removable lens.

18. A method for forming an optical lens stack for attachment to an airfoil, the method comprising the steps of:

a) laminating together a multiplicity of optical lens layers while interposing an uninterrupted adhesive layer between each optical lens layer being laminated;

b) forming a tab extension from each optical lens layer and omitting the adhesive layer from the tab extension, whereby each of the lens layers can be peeled off individually; and c) cutting around the perimeter and to a depth of one optical lens ply the bottom-most layer of the optical stack, thereby exposing a strip of adhesive for adhering the optical stack to the airfoil.

19. The stack of laminated removable lenses recited in claim 1, wherein there is an optical index matching of about 0.2 between each said removable lens and the uninterrupted layer interposed between said removable lens and the successive removable lens.

* * * * *